United States Patent [19]
Cragoe, Jr. et al.

[11] 4,055,597
[45] Oct. 25, 1977

[54] 10-AZA-11,12-SECOPROSTAGLANDINS

[75] Inventors: Edward J. Cragoe, Jr.; John B. Bicking, both of Lansdale, Pa.

[73] Assignee: Merck & Co., Inc., Rahway, N.J.

[21] Appl. No.: 583,075

[22] Filed: June 2, 1975

Related U.S. Application Data

[63] Continuation-in-part of Ser. No. 326,934, Jan., 1973, abandoned.

[51] Int. Cl.$^2$ .............................................. C07C 101/00
[52] U.S. Cl. ..................... 260/534 M; 260/429.9; 260/439 R; 260/448 R; 260/501.11; 260/539 R; 260/561 B; 260/561 H; 260/632 Y; 260/633; 424/287; 424/289; 424/295; 424/311; 424/316; 424/319; 560/170; 560/187; 560/190; 560/252; 560/253; 560/251; 560/266; 560/262; 560/180; 560/226

[58] Field of Search .......... 260/534 M, 448 R, 439 R, 260/429.9

[56] References Cited
PUBLICATIONS

Tetrahydrodon Letters, No. 42, pp. 3719–3728, (1965).
Wagner et al., "Synthetic Organic Chemistry" (1953), p. 566.

*Primary Examiner*—Joseph E. Evans
*Attorney, Agent, or Firm*—Thomas E. Arther; Harry E. Westlake, Jr.; Rudolph J. Anderson, Jr.

[57] ABSTRACT

This invention relates to 10-aza-11,12-secoprostaglandins and processes for their manufacture. These compounds have prostaglandin-like biological activity and are particularly useful as renal vasodilators.

14 Claims, No Drawings

10-AZA-11,12-SECOPROSTAGLANDINS

RELATIONSHIP TO OTHER APPLICATIONS

This application is a continuation-in-part of copending United States application Ser. No. 326,934, filed Jan. 26, 1973 now abandoned.

SUMMARY OF THE INVENTION

This invention relates to novel 10-aza-11,12-secoprostaglandins. These compounds can be represented by the following structural formula:

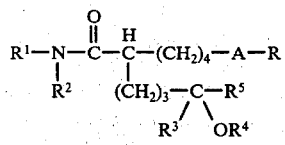

I wherein R is selected from the group consisting of carboxy and a carboxy salt being formed from a pharmaceutically acceptable cation, such as metal cations derived from alkali metals, alkaline earth metals, and amines such as ammonia, primary and secondary amines, and quarternary ammonium hydroxides. Especially preferred metal cations are those derived from alkali metals, e.g., sodium, potassium, lithium, and the like, and alkaline earth metals, e.g., calcium, magnesium and the like, and other metals, i.e. aluminum, iron, and zinc.

Pharmaceutically acceptable cations derived from primary, secondary, or tertiary amines, or quaternary ammonium hydroxides are methylamine, dimethylamine, trimethylamine, ethylamine, N-methylhexylamine, benzylamine, α-phenethylamine, ethylenediamine, piperidine, morpholine, pyrrolidine, 1,4-dimethylpiperazine, ethanolamine, diethanolamine, triethanolamine, tris(hydroxymethyl)aminomethane, N-methylglucamine, N-methylglucosamine, ephedrine, procaine, tetramethylammonium hydroxide, tetraethylammonium hydroxide, benzyltrimethylammonim and the like.

R is selected from alkoxycarbonyl (—COOR$^6$) wherein R$^6$ is alkyl having 1-10 carbon atoms, carbamoyl (—CONH$_2$); substituted carbamoyl (—CONR$^7$R$^8$) wherein R$^7$ and R$^8$ are selected from the group consisting of hydrogen, lower alkyl having 1-4 carbon atoms and diloweralkylaminoalkyl having 4-7 carbon atoms; and carbazoyl (—CONHNH$_2$).

A is selected from the group consisting of ethylene (—CH$_2$CH$_2$—), trimethylene (—CH$_2$CH$_2$CH$_2$—), α-methylethylene (—CH$_2$CH(CH$_3$)—), β-methylethylene (—CH(CH$_3$)CH$_2$—), α,α-dimethylethylene (—CH$_2$—C(CH$_3$)$_2$—), β,β-dimethylethylene (—C(CH$_3$)$_2$CH$_2$—) and oxymethylene (—O—CH$_2$—). (Note that when A consists of a two carbon bridge, the term "α" refers to the other carbon atom.)

R$^1$ is selected from the group consisting of hydrogen and methyl.

R$^2$ is selected from the group consisting of hydrogen, methyl, ethyl and propyl.

R$^3$ is selected from the group consisting of hydrogen and methyl.

R$^4$ is selected from the group consisting of hydrogen and lower alkanoyl of 1-5 carbon atoms, e.g., formyl, acetyl, propionyl, buatyryl, isobutyryl, valeryl, pivaolyl and the like.

R$^5$ is selected from the group consisting of lower alkyl of 3-7 carbon atoms either straight or branched chain (e.g., propyl, isopropyl, butyl, tertbutyl, pentyl 1,1-dimethylpentyl, 4-methylpentyl, 4,4-dimethylpentyl, hexyl, heptyl), 4-pentenyl, and 5,5,5-trifluoropentyl; except that when R$^3$ is methyl, R$^5$ cannot be 4-pentenyl.

A preferred embodiment of this invention relates to the 10aza-11,12-secoprostaglandins having the following general formula:

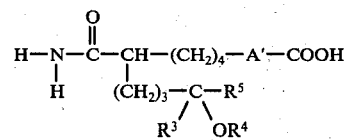

II wherein A' is ethylene or oxymethylene; and R$^3$, R$^4$, and R$^5$ are as defined above.

It is to be noted that the carbon bearing R$^3$ and OR$^4$ is asymmetric. This invention covers stereoisomers in which this asymmetric center is exclusively in either one or the other of the two possible configurations, R and S.

BACKGROUND OF THE INVENTION

The compounds of formula I are described as 10-aza-11,12-secoprostaglandins because of their structural relationship to the naturally occurring prostaglandins.

The prostaglandins constitute a biologically prominent class of naturally occurring, highly functionalized C$_{20}$ fatty acids which are anabolized readily in a diverse array of mammalian tissues from three essential fatty acids; namely, 8,11,14-eicosatrienoic acid, 5,8,11,14-eicosatetraenoic acid and 5,8,11,14,17-eicosapentaenoic acid. Each known prostaglandin is a formal derivative of the parent compound, termed "prostanoic acid"; the latter is a C$_{20}$ fatty acid covalently bridged between carbons 8 and 12 such as to form a trans, vicinally-substituted cyclopentane in which the carboxy-bearing side chain is "alpha" or below the plane of the ring and the other side chain is "beta" or above the plane of the ring as depicted in formula III:

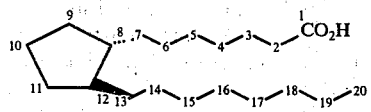

III

The six known primary prostaglandins, PGE$_1$, PGE$_2$, PGE$_3$, PGF$_{1\alpha}$, PGF$_{2\alpha}$, and PGF$_{3\alpha}$ resulting directly from anabolism of the above cited essential fatty acids via the action of prostaglandin synthetase, as well as the three prostaglandins resulting from in vivo dehydration of the PGE's, i.e., PGA$_1$, PGA$_2$, and PGA$_3$, are divided into three groups; namely, the PGE, PGF, and PGA series on the basis of three distinct cyclopentane nuclear substitution patterns as illustrated as follows:

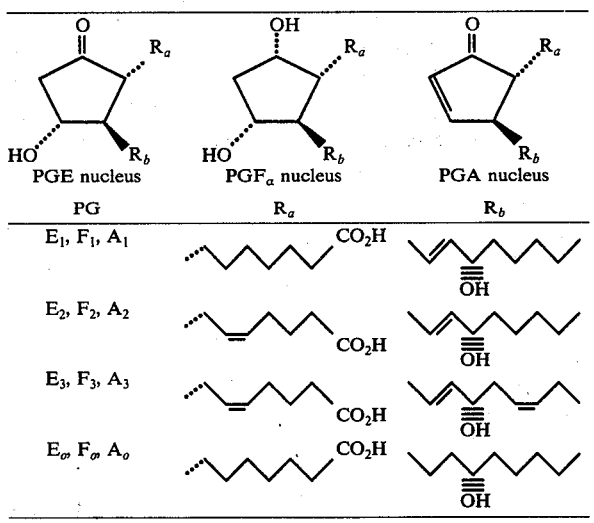

It should be noted that the Arabic subscripts designate the number of carbon-carbon double bonds in the designated compound and that the Greek subscript used in the PGF series designates the stereochemistry of the C-9 hydroxyl group.

Although the prostaglandins were discovered independently in the mid-1930's by Goldblatt [J. Chem. Soc. Chem. Ind. Lond., 52, 1056 (1933)] in England and Von Euler [Arch. Exp. Path. Pharmark., 175, 78 (1934)] in Sweden, these complex natural products received little attention from the scientific community until the early 1960's which coincides with the advent of modern instrumentation (e.g., mass spectrometry) which, in turn, was requisite for their successful isolation and structural elucidation by Bergström and colleagues [see Angew, Chem. Int. Ed., 4, 410 (1965) and references cited therein for an account of this work]. Within the last decade, a massive international scientific effort has been expended in developing both biosynthetic and chemical routes to the prostaglandins and, subsequently, in investigating of their biological activities. During this period, prostaglandins have been shown to occur extensively in low concentrations in a myriad of mammalian tissues where they ae both rapidly anabolized and catabolized and to exhibit a vast spectrum of pharmacological activities including prominent roles in (a) functional hyperemia, (b) the inflammatory response, (c) the central nervous system, (d) transport of water and electrolytes, and (e) regulation of cyclic AMP. Further details concerning the prostaglandins can be found in recent reviews of their chemistry [J. E. Pike, Fortschr. Chem. Org. Naturst., 28, 313 (1970) and G. F. Bundy, A. Rep. in Med. Chem., 7, 157 (1972)], biochemistry [J. W. Hinman, A. Rev. Biochem., 41, 161 (1972)], pharmacolgly [J. R. Weeks, A. Rev. Pharm., 12, 317 (1972)], physiological significance [E. W. Horton, Physiol, Rev., 49, 122 (1969)] and general clinical application (J. W. Hinman, Postgrad. Med. J., 46, 562 (1970].

The potential application of natural prostaglandins as medicinally useful therapeutic agents in various mammalain disease states is obvious but suffers from three formidable major disadvantages, namely, (a) prostaglandins are known to be rapidly metabolized in vivo in various mammalian tissues to a variety of metabolites which are devoid of the desired original biological activities, (b) the natural prostaglandins are inherently devoid of biological specificity which is requisite for a successful drug, and (c) although limited quantities of prostaglandins are presently produced by both chemical and biochemical processes, their production cost is extremely high; and, consequently, their availability is quite restricted.

Our interest has, therefore, been to synthesize novel compounds structurally related to the natural prostaglandins but with the following unique advantages: (a) simplicity of synthesis leading to low cost of production; (b) specificity of biological activity which may be either of a prostaglandin-mimicking or prostaglandin-antagonizing type; (c) enhanced metabolic stability. The combination of these advantages serves to provide effective, orally and parenterally active therapeutic agents for the treatment of a variety of human and animal diseases. Included are applications in renal, cardiovascular, gastrointestinal, respiratory, and reproductive systems, and in the control of lipid metabolism, inflammation, blood clotting, skin diseases, and certain cancers.

More specifically, in the clinic, prostaglandin agonists can function as agents for improving renal function (e.g., renal vasodilation), antihypertensives, anti-ulcer agents, agents for fertility control, antithrombotics, antiasthmatics, antilipolytics, antineoplastic agents, and agents for the treatment of hypersensitivity and certain skin diseases.

Prostaglandin antagonists can function as anti-inflammatory agents, anti-diarrheal agents, antipyretics, agents for prevention of premature labor, and agents for the treatment of headache.

The compounds of the present invention are useful as pharmaceutically active compounds. Thus, these compounds are orally active in the treatment of conditions which are responsive to the actions of the natural prostaglandins. It is of course necessary to determine by routine laboratory testing which of the compounds of the present invention are most suitable for a specific end use. The compounds of this invention have prostaglandin-like activity in that they mimic the effect of prostaglandin $E_1$ in stimulating the formation of cyclic AMP in the mouse ovary in vitro.

The compounds of this invention are particularly useful for improving renal function. Certain of the compounds of this invention, e.g., 8-carbamoyl-12-hydroxyheptadecanoic acid, mimic the effects of prostaglandin $E_1$; and thus are useful on oral administration in producing increased renal blood flow (renal vasodilation) in laboratory animals and are useful in improving renal function in animals, for example, dogs, with poorly-functioning kidneys.

Becaue of their biological activity and ready accessibility, the compounds of the invention are also useful in that they permit large scale animal testing useful and necessary to understanding of these various disease conditins, such as kidney impairment, ulcers, dwarfism caused by poorly-functioning pituitary glands, stroke (thrombus formation), and the like. It will be appreciated that not all of the compounds of this invention have these biological activities to the same degree but the choice of any particular ones for any given purpose will depend upon several factors including the disease state to be treated.

The compounds of this invention can be aadministered either topically or systemically, i.e., intravenously, subcutaneously, intramuscularly, orally, rectally, or by aerosolization in the form of sterile implants for long action.

Whatever the mode of administation, doses in the range of about 0.10 to 20 milligrams per kilogram of body weight per day are used. The exact dose depends on the age, weight, and condition of the patient, and the frequency and route of administration.

The low cost and ready accessibility of the compounds of this invention make them particularly promising for applications in veterinary medicine in which field their utilities are comparable to those in human medicine.

PROCESS TO PREPARE THE COMPOUNDS

In preparing the new chemical compounds with which this invention is concerned, we have found it desirable to use as starting materials the following acid chloride compounds:

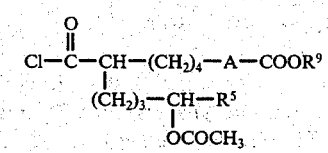   III

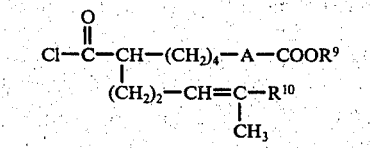   IV wherein $R^9$ is loweralkyl having 1-5 carbon atoms, preferably ethyl; $R^{10}$ is loweralkyl of 3-7 carbon atoms being straight or branched, and 5,5,5-trifluoropentyl; and $R^5$ and A are as defined in formula I above.

Compound III, above, after further reactions as hereinafter described, yields final products wherein $R^3$ is hydrogen and the rest of the substituents are as defined in formula I. Compound IV yields final products as defined in formula I wherein $R^3$ is methyl and the rest of the substituents are as defined, with the exception that $R^5$ cannot be 4-pentenyl. In other words, when $R^3$ is methyl, $R^5$ in formula I is loweralkyl of 3-7 carbon atoms, or 5,5,5-trifluoropentyl.

These starting materials III and IV do not form a part of this invntion but are disclosed in a co-pending United States application, Ser. No. 302,365, filed Oct. 30, 1972 in the names of Cragoe, Bicking, and Smith and now abandoned. Procedures for their preparation are given hereinafter.

The starting materials III and IV are reacted with an amine of the formula:

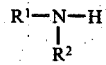   V wherein $R^1$ is hydrogen or methyl, and $R^2$ is hydrogen or loweralkyl of 1-3 carbon atoms. To prepare compounds of formula I wherein both $R^1$ and $R^2$ are hydrogen, ammonia (VI)

   VI is used in the reaction with the acid chloride starting materials III or IV.

The reaction between the acid chloride III or IV and the compound V or VI is conducted by adding the acid chloride to a previously prepared aqueous solution of the amine or ammonia. This reaction is conducted at ambient temperature. The amide reaction product precipitates and is collected and treated as necessary to yield the ultimate products. For instance, when the acid chloride IV is the chosen starting material, the next step following reaction with the amine is a hydration step wherein the elements of water are added across the double bond. This is effected using the following oxymercuration-demercuration process.

The compound:

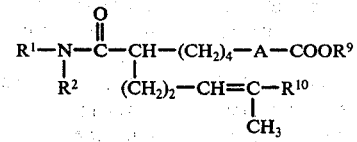   VII wherein $R^1$, $R^2$, $R^9$, $R^{10}$, and A are as defined in compound IV, is treated with mercuric acetate in aqueous tetrahydrofuran for a prolonged period to effect oxymer-curation followed by treatment of the reaction mixture with sodium borohydride to effect demercuration. The product of this process is compound VIII:

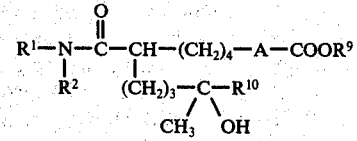   VIII

Mild basic hydrolysis (NaOH is aqueous methanol or ethanol) of the ester function of compound VIII yields compounds of formula I, i.e., IX:

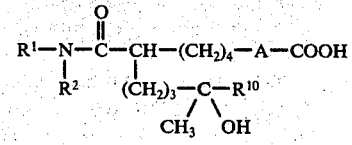   IX

When the acid chloride III is the chosen starting material, the reaction product is:

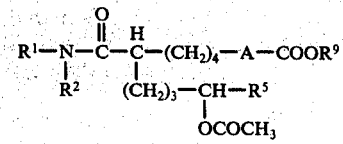   X

When compound X is submitted to mild basic hydrolysis (preferably a dilute solution of NaOH in aqueous methanol or ethanol), both blocking groups ($R^9$ and the —COCH$_3$ group) are removed simultaneously, yielding the following compounds of formula I, i.e., XI:

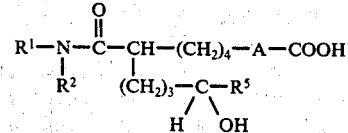   XI

It is frequently advantageous from a therapeutic standpoint to prepare compounds of this invention (formula I) in which the asymmetric carbon atom which bears $R^3$ and $OR^4$ is exclusively in the R or S configuration. It will be recalled that the corresponding center in the natural prostaglandins is in the S configuration; inversion of this center usually produces a reduction in biological activity, although sometimes a marked increase in biological specificity results.

In our series of 10-aza-11,12-secoprostaglandins, compounds exclusively R or S at this center can be produced by employing an acid chloride III which itself is in the R or S configuration at this center.

The preparation of the pre-resolved acid chloride in not a part of this invention, but the methodology is disclosed in co-pending United States application, Ser. No. 302,365, filed Oct. 30, 1972 in the names of Cragoe, Bicking, and Smith. This synthesis is discussed in more detail hereinafter in the section "Preparation of Starting Materials".

DERIVATIZATION OF PRODUCTS

The directly obtained products of the process described supra can be derivatized to yield the other products of formula I.

1. The fundamental process yields compounds where R is carboxy. To obtain carboxy salts the acid products are dissolved in a solvent such as ethanol, methanol, glyme and the like and the solution treated with an appropriate alkali or alkaline earth hydroxide or alkoxide to yield the metal salt, or with an equivalent quantity of ammonia, amine or quaternary ammonium hydroxide to yield the amine salt. In each instance, the salt either separates from the solution and may be separated by filtration or, when the salt is soluble it may be recovered by evaporation of the solvent. Aqueous solutions of the carboxylic acid salts can be prepared by treating an aqueous suspension of the carboxylic acid with an equivalent amount of an alkaline earth hydroxide or oxide, alkali metal hydroxide, carbonate or bicarbonate, ammonia, an amine or a quaternary ammonium hydroxide.

To obtain carboxy esters (i.e., compounds where R is alkoxycarbonyl) the acid products are treated in ether with an ethereal solution of the appropriate diazoalkane. For example, methyl esters are produced by reaction of the acid products with diazomethane. To obtain products where R is carbamoyl, substituted carbamoyl or carbazoyl the acid product is first converted to an active Woodward ester. For example, the acid product can be made to react with N-tert-butyl-5-methylisoxazolium perchlorate in acetonitrile in the presence of a base such as triethylamine to yield an active ester in which R is

Active esters of this type can be reacted with ammonia to yield products of formula I where R is carbamoyl, with primary or secondary amines or di-lower-alkylaminoalkylamines to yield products where R is substituted carbamoyl, i.e., $-CONR^7R^8$, and with hydrazine to yield products where R is carbazoyl.

2. The fundamental process yields products where $R^4$ is hydrogen. In compounds of formula XI (in which $R^3$ is hydrogen), reaction with formic acid, acetic anhydride, propionic anhydride, butyric anhydride, isobutyric anhydride, valeric anhydride, pivalic anhydride and the like, without solvent and at temperatures from 25° to 60° C., gives compounds wherein $R^4$ is formyl, acetyl, propionyl, butyryl, isobutyryl, valeryl, and pivaloyl, respectively.

PREPARATION OF STARTING MATERIALS

1. Acid Chlorides of Formulas III and IV

The starting material to prepare these compounds is di-tert-butyl malonate. This ester is treated with an equivalent of base such as sodium hydride, sodium ethoxide, sodium amide, or the like. The enolate anion thus produced is alkylated with a compound of the formula:

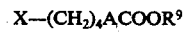
XII wherein X is a halogen atom, preferably bromine or chloride, A is as defined in formula I, and $R^9$ is lower alkyl having 1-5 carbon atoms, preferably ethyl. This reaction is conducted in an inert solvent or solvent system such as dimethylformamide, dimethylformamide-benzene (1:1) or diglyme, at a temperature ranging from 40° to 120° C. The reactants are employed in approximately equimolar amounts. The reaction is complete in 2-4 hours.

The intermediate compound prepared is then treated with an equimolar amount of base such as NaH, $NaOC_2H_5$, or $NaNH_2$ and then alkylated with either of the following reagents XIIIA or XIIIB:

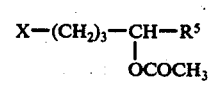
XIIIA

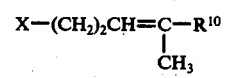
XIIIB

At this point, the compounds XIV and XV are obtained:

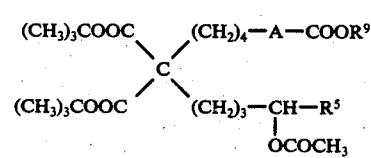
XIV

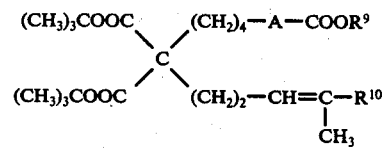
XV

Either of these compounds is heated in an inert solvent with a trace of acid to effect elimination of isobutylene and decarboxylation. Compounds XVI and XVII are obtained, respectively:

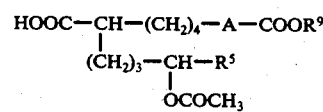
XVI $$\text{HOOC—CH—(CH}_2)_4\text{—A—COOR}^9 \quad \text{XVII}$$
$$|$$
$$(\text{CH}_2)_2\text{—CH=C—R}^{10}$$
$$|$$
$$\text{CH}_3$$

In turn, either of these compounds is heated with thionyl chloride at 60° to 120° C. for 2 to 6 hours in an inert solvent (e.g., benzene, toluene) to yield the acid chloride starting compounds III and IV.

2. Pre-Resolved Acid Chloride of Formula III

As was noted previously, the pre-resolved acid chloride in the R or S configuration is a useful starting material to yield final products having the desired optical configuration.

The same general synthetic scheme as described at paragraph 1, above, is used, except that the reagent XIIIC is used instead of either XIIIA or XIIIB:

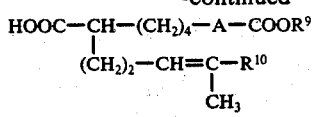

XIIIC

In compound XIIIC, W indicates halogen, mesyl, or tosyl, $R^{10}$ is loweralkyl of 3-7 carbons, or 2,2,2-trifluoroethyl, the carbon atom marked with an asterisk is exclusively in the R or S configuration.

The use of this compound XIIIC gives the intermediate XVIII:

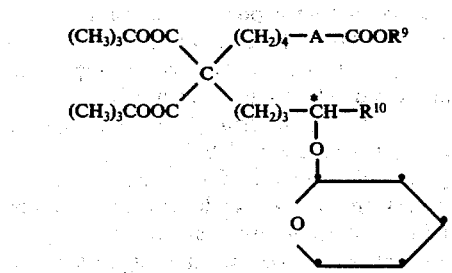

XVIII which can be converted to the acid chloride XIX by the series of chemical reactions as follows:

a. Intermediate XVIII is treated with dilute hydrochloric acid in tetrahydrofuran solution to effect removal of the tetrahydropyranyl protecting group;

b. The hydroxyl group of the resulting product is re-protected by acetylation; acetic anhydride is employed.

c. The resulting intermediate in which acetyl replaces the tetrahydropyranyl moiety of XVIII is heated in an inert solvent with a trace of strong acid to effect elimination of 2 moles of isobutylene and decarboxylation; and d. The resulting carboxylic acid is converted to the acid chloride XIX by the action of thionyl chloride.

XIX $$\text{O}$$
$$\parallel$$
$$\text{Cl—C—CH—(CH}_2)_4\text{—A—COOR}^9$$
$$|$$
$$(\text{CH}_2)_3\text{—}\overset{*}{\text{C}}\text{H—R}^{10}$$
$$|$$
$$\text{OCOCH}_3$$

PREPARATION OF REAGENTS FOR STARTING MATERIALS

1. The reagent XIIIA which has the following general formula wherein X is halogen, and $R^5$ is as defined previously is prepared in the following manner:

XIIIA $$\text{X—(CH}_2)_3\text{—}\overset{*}{\text{C}}\text{H—R}^5$$
$$|$$
$$\text{OCOCH}_3$$

A Grignard reagent $R^5MgI$ or $R^5MgBr$ is allowed to react in ether or tetrahydrofuran with a nitrile $X(CH_2)_3CN$. The immediately resulting imine is hydrolyzed in aqueous acidic solution to give ketones of the formula $X(CH_2)_3C(=O)-R^5$. The ketones are reduced to the alcohols $X(CH_2)_3-CH(OH)-R^5$ with sodium or potassium borohydride in a suitable solvent such as methanol, ethanol or diglyme. Acetylation of these alcohols preferably with acetic anhydride yields the reagent XIIIA.

2. The reagent XIIIB which has the following general formula wherein X is halogen, and $R^{10}$ is as defined previously:

XIIIB $$\text{X—(CH}_2)_2\text{CH=C—R}^{10}$$
$$|$$
$$\text{CH}_3$$

is prepared as follows:

A Grignard reagent $R^{10}MgBr$ or $R^{10}MgI$ is allowed to react with haloketones $X(CH_2)_3-C(=O)CH_3$ to give, after hydrolysis, the tertiary alcohol $X(CH_2)_3-C(OH)-(CH_3)-R^{10}$. This alcohol can be dehydrated by treatment with a variety of acidic reagents and with heat to give the reagent XIIIB. A preferred method of dehydration involves acetylation of the alcohols with acetic anhydride, and then heating the resulting esters in an inert solvent (benzene, toluene, or the like) at from 80° to 140° C. in the presence of a trace of an acid such as sulfuric or p-toluenesulfonic acid to effect elimination of acetic acid.

3. The optically active reagent XIIIC is prepared (where the optical center is indicated by a star)

XIIIC

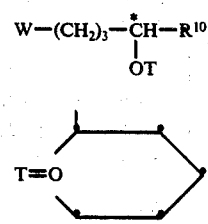

by a process described as follows:

An aldehyde $R^{10}-CHO$ is caused to react preferably in tetrahydrofuran with ethynylmagnesium bromide to give a 1-alkyn-3-ol, HC≡C—ĊH(OH)—R¹⁰. This racemic alcohol is resolved preferably by formation of the acid phthalate ester, salt formation of the latter with an optically active base [(−) or (+)-α-methylbenzylamine, or (−) or (+)-amphetamine (for example)], and separation of the diastereomeric salts by fractional crystallization. These salts are treated with dilute aqueous acid to give the optically active acid phthalate esters, and then hydrolyzed in dilute aqueous alkali (for example, 10% NaOH, 30 min. at 60°) to give the separated R and S isomers of the 1-alkyn-3-ols, HC≡C—ĊH(OH)—R¹⁰.

These optically active alcohols are then (a) converted to the optically active, tetrahydropyranyl protected, 1-alkyn-3-ols by reaction with dihydropyran; (b) the products are converted to the acetylenic Grignard reagents and caused to react with triethyl orthoformate to give $(C_2H_5O)_2CH$—C≡C—ĊH(OT)—R¹⁰; (c) these acetals are hydrolyzed in aqueous acid to give OCH—C≡C—ĊH(OH)—R¹⁰; (d) these products are protected by reaction with dihydropyran; (e) and the triple bond of the resulting compounds reduced by catalytic hydrogenation to yield $O=CHCH_2CH_2\overset{*}{C}H(OT)$—R¹⁰.

These aldehydes are reduced to the alcohols $HOCH_2CH_2CH_2\overset{*}{C}H(OT)$—R¹⁰ by reaction with sodium or potassium borohydride preferably in diglyme (diethylene glycol dimethyl ether) solution at temperatures from 10°–40° C. The alcohols are caused to react with methanesulfonyl chloride or p-toluenesulfonyl chloride in pyridine solution at 0°–30° C. to give intermediates of formula XIIIC where W is methanesulfonyloxy or p-toluenesulfonyloxy, respectively. These mesylates and tosylates can be reacted with sodium iodide in acetone solution to give intermediates XIIIC where W is iodo.

4. The preparation of reagents of formula XII has been described in the scientific and patent

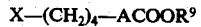   X—(CH₂)₄—ACOOR⁹   XII literatures in instances where A is ethylene, trimethylene, α-methylethylene, β-methylethylene, α,α-dimethylethylene, β,β-dimethylethylene. To prepare reagents where A is oxymethylene, an ester of glycolic acid, HOCH₂COOR⁹ is treated with a strong base, preferably sodium hydride, in a non-protic solvent (dimethylformamide, glyme, and the like) and the resulting anion caused to react with a 1,4-dihalobutane, preferably 1,4-dibromobutane. The glycolic ester and base are employed in approximately equimolar quantities; a 1.5 to 2 molar excess of the dihalobutane is advantageously used.

5. Methods for obtaining optical antipodes of some compounds of this invention have been described supra in paragraph 3 whereby one of the components of the molecule is preresolved prior to its assembly into the whole molecule. Other methods also can be employed; for example, mixtures of racemates may be separated by taking advantage of the physiochemical differences between the components using chromatography and/or fractional crystallization. The racemic products and intermediates of this invention can be resolved into their optically active components by any one of a number of methods of resolution which are well described in the chemical literature.

Those compounds which are carboxylic acids can be converted to the diastereoisomeric salts by treatment with an optically active base such as + or − α-methylbenzylamine, + or − α-(1-naphthyl)-ethylamine, brucine, cinchonine, cinchonidine, or quinine. These diastereoisomeric salts can be separated by fractional crystallization.

The carboxylic acids of this invention also can be converted to esters using an optically active alcohol, such as, estradiol-3-acetate, or d- or l-menthol and the diastereoisomeric esters resolved by crystallization or by chromatographic separation.

Racemic carboxylic acids also may be resolved by reverse phase and absorption chromatography using an optically active support and absorbent.

Compounds of this invention which contain free hydroxyl groups can be esterified with acid chlorides or anhydrides derived from optically active acids, such as, (+)-10-camphorsulfonic acid, (+)-α-bromocamphor-π-sulfonic acid, or d- or 1-6,6'-dinitrodiphenic acid to form esters which can be resolved by crystallization.

Another method of obtaining pure optical isomers involves incubation of the racemic mixture with certain microorganisms such as fungi, by processes well established in the art, and recovering the product formed by the enzymatic transformation.

The methods described supra are especially effective if one applies the process to a compound where one asymmetric center has been preresolved by the techniques alreaady described.

This invention is further described in the following examples.

PREPARATION OF INTERMEDIATES

A. Preparation of 1-Chloro-4-acetoxynonane

Step 1. Preparation of 1-Chloro-4-nonanone

To the Grignard reagent prepared from a mixture of amyl bromide (226.59 g.; 1.5 moles) and magnesium (36.48 g.; 1.5 moles) in ether (1000 ml.) is added, dropwise, during one hour, 4-chlorobutyronitrile (155.34 g.; 1.5 moles). Stirring is continued for an additional one hour. The reaction mixture is poured into a mixture of finely crushed ice (1000 g.) and concentrated hydrochloric acid (750 ml.). The ether layer is separated quickly and discarded. The aqueous layer is heated on a steam bath for one hour to hydrolyze the intermediate imine and cause the separation of the ketone as an oil. After cooling, the oil is extracted with ether and the combined extracts are washed with saturated sodium chloride solution and dried over anhydrous sodium sulfate. The solvent is removed under vacuum and the residual oil is distilled to give 69.0 g. (26%) of colorless oil, b.p. 115°–117°/14 mm.; pmr (CDCl₃) δ0.90 (3H,t), 3.56 (2H,t,CH₂Cl).

Step 2. Preparation of 1-Chloro-4-nonanol

A suspension of sodium borohydride (6.62 g.; 0.175 mole) and sodium hydroxide (1.3 g.) in ethanol (310 ml.) is treated, dropwise, over 1 hour with 1-chloro-4-nonanone (61.40 g.; 0.349 mole) while the temperature is maintained at 45°–50°. Stirring is continued for one hour, longer without external cooling.

The reaction mixture is acidified with concentrated hydrochloric acid to the Congo red endpoint and then the ethanol is removed under reduced pressure. The residue is treated with water (200 ml.) and the resulting oil is extracted with ether. The combined extracts are washed with saturated sodium chloride solution and dried over anhydrous sodium sulfate. The solvent is removed under vacuum to give the title compound as a light yellow residual oil, yield 58.85 g.; ir (neat) 3400 cm$^{-1}$.

Step 3. Preparation of 1-Chloro-4-acetoxy-nonane

A mixture of 1-chloro-4-nonanol (111.99 g.; 0.627 mole) and acetic anhydride (128.0 g.; 1.254 moles) is heated on a steam bath for 1½ hours.

The volatile materials are removed under reduced pressure and the residual oil is distilled to give 88.6 g. (64%) of colorless oil, b.p. 130°–133°/14 mm.; pmr (CDCl$_3$) δ0.89 (3H,t), 2.02 (3H,s CH$_3$COO), 3.53 (2H,t CH$_2$Cl), 4.89 (1H,m). Anal. Calcd. for C$_{11}$H$_{21}$ClO$_2$: C, 59.85, H, 9.59. Found: C, 59.87; H, 9.67.

B. Preparation of 1-Chloro-4-acetoxy-8-methylnonane

Step 1. Preparaion of 1-Chloro-8-methyl-4-nonanone

To the Grignard reagent prepared from a mixture of 1-bromo-4-methylpentane (200.00 g.; 1.21 mole) and magnesium (29.43 g.; 1.21 mole) in ether (800 ml.) is added, dropwise during one hour, 4-chlorobutyronitrile (125.30 g.; 1.21 mole). Stirring is continued for an additional one hour.

The reaction mixture is poured into a mixture of finely crushed ice (800 g.) and concentrated hydrochloric acid (600 ml.). The ether layer is separated quickly and discarded. The aqueous layer is heated on a steam bath for one hour to hydrolyze the intermediate imine and cause the separation of the ketone as an oil. After cooling, the oil is extracted with ether and the combined extracts are washed with saturated sodium chloride solution and dried over anhydrous sodium sulfate. The solvent is removed under vacuum and the residual oil is distilled to give 23.3 g. (10%) of colorless oil, b.p. 121°–122°/15 mm.; pmr (CDCl$_3$)δ0.89 (6H,d), 3.57 (2H,t CH$_2$Cl).

Anal. Calcd. for C$_{10}$H$_{19}$ClO: C, 62.98; H, 10.04. Found: C, 62.86; H, 10.20.

Step 2. Preparation of 1-Chloro-8-methyl-4-nonanol

A suspension of sodium borohydride (2.3 g., 0.061 mole) and sodium hydroxide (0.5 g.) in ethanol (110 ml.) is treated dropwise during one hour with 1-chloro-8-methyl-4-nonanone (23.0 g., 0.121 mole) while the temperature is maintained at 45°–50° C. Stirring is continued for one hour longer without external cooling.

The reaction mixture is acidified with concentrated hydrochloric acid to the Congo Red endpoint and then the ethanol is removed under reduced pressure. The residue is treated with water (70 ml.) and the resulting oil is extracted with ether. The combined extracts are washed with saturated sodium chloride solution and dried over anhydrous sodium sulfate. The solvent is removed under vacuum to give the title compound as a light yellow residual oil, yield 22.73 g.; ir (neat) 3400 cm$^{-1}$.

Step 3. Preparation of 1-Chloro-4-acetoxy-8-methylnonane

A mixture of 1-chloro-8-methyl-4-nonanol (22.73 g.; 0.118 mole) and acetic anhydride (24.07 g.; 0.236 mole) is heated on a steam bath for 1½ hours.

The volatile materials are removed under reduced pressure and the residual oil is distilled to give 14.58 g. (58%) of colorless oil, b.p. 138°–139°/15 mm.; pmr (CDCl$_3$)δ0.85 (6H,d), 2.02 (3H,s CH$_3$COO), 3.53 (2H,t CH$_2$Cl), 4.92 (1H,m).

C. Preparation of 1-Chloro-4-acetoxyundecane

Step 1. Preparation of 1-Chloro-4-undecanone

This compound is prepared essentially by the same procedure as described for 1-chloro-4-nonanone (Example A, Step 1) using the following reagents:

1-Bromoheptane: 214.94 g. (1.2 mole)
Mgnesium: 29.18 g. (1.2 mole)
Ether: 800 ml.
4-Chlorobutyronitrile: 124.27 g. (1.2 mole)

The title compound is obtained as a colorless oil, yield 60.4 g. (15%), b.p. 135°–140°/15 mm.; pmr (CDCl$_3$)δ0.93, (3H,t), 3.57 (2H,t CH$_2$Cl).

Step 2. Preparation of 1-Chloro-4-undecanol

This compound is prepared essentially by the same procedure as described for 1-chloro-4-nonanol (Example A, Step 2) using the following reagents:

Sodium borohydride: 5.56 g. (0.147 mole)
Sodium hydroxide: 1.12 g.
Ethanol: 265 ml.
1-Chloro-4-undecanone: 60.00 g. (0.294 mole)

The title compound is obtained as a yellow residual oil, yield 60.02 g.

Step 3. Preparation of 1-Chloro-4-acetoxy-undecane

This compound is prepared essentially by the same procedure as described for 1-chloro-4-acetoxy-nonane (Example A, Step 3), using the following reagents:

1-Chloro-4-undecanol: 60.02 g. (0.29 mole)
Acetic anhydride: 59.16 g. (0.58 mole)

The title compound is obtained as a colorless oil, yield 44.6 g. (62%), b.p. 155°–158°/15 mm.; pmr (CDCl$_3$)δ0.88 (3H,t), 2.02 (3H,s CH$_3$COO), 3.53 (2H,t CH$_2$Cl), 4.92 (1H,m).

Anal. Calcd. for C$_{13}$H$_{25}$ClO$_2$: C, 62.76; H, 10.13. Found: C, 63.03; H, 10.40.

D. Preparation of 1-Chloro-4-acetoxy-8,8-dimethylnonane

By following the procedure described for 1-chloro-4-acetoxynonane (Example A) but substituting 1-bromo-4,4-dimethylpentane for amyl bromide, there is obtained in succession: 1-chloro-8,8-dimethyl-4-nonanone, 1-chloro-8,8-dimethyl-4-nonanol, and 1-chloro-4-acetoxy-8,8-dimethylnonane.

E. Preparation of 1-Chloro-4-acetoxy-9,9,9-trifluorononane

By following the procedure described for 1-chloro-4-acetoxynonane (Example A) but substituting 1-bromo-5,5,5-trifluoropentane for amyl bromide, there is obtained in succession: 1-chloro-9,9,9-trifluoro-4-nonanone, 1-chloro-9,9,9-trifluoro-4-nonanol, and 1-chloro-4-acetoxy-9,9,9-trifluorononane.

F. Preparation of 1-Chloro-4-acetoxy-8-nonene

By following the procedure described for 1-chloro-4-acetoxynonane (Example A) but substituting 1-bromo-4-pentene for amyl bromide, thre is obtained in succession: 1-chloro-8-nonen-4-one, 1-chloro-8-nonen-4-ol, and 1-chloro-4-acetoxy-8-nonene.

G. Preparation of 1-Chloro-4-acetoxy-5,5-dimethylnonane

Step 1. Preparation of 1-Chloro-5,5-dimethyl-4-nonanone

Four hundred ml. of a solution in ether of 1,1-dimethylpentylmagnesium chloride prepared from magnesium (24.3 g., 1.0 mole) and 1-chloro-1,1-dimethylpentane (134.5 g., 1.0 mole) according to the procedure of Whitmore and Badertscher [J. Am. Chem. Soc., 55, 1559 (1933)] is added dropwise with stirring to 4-chlorobutyryl chloride (197 g., 1.4 moles) in ether (400 ml.) during 6 hours. The reaction mixture is stirred for an additional 12 hours. It is then poured into a mixture of ice and dilute hydrochloric acid. The ether layer is separated, washed with water and brine and dried over sodium sulfate. The ether is evaporated and the residue distilled at aspirator vacuum through a Vigreaux column to yield the product as a colorless oil.

Step 2. Preparation of 1-Chloro-5,5-dimethyl-4-nonanol

By following the procedure described for 1-chloro-4-nonanol (Example A, Step B) but substituting 1-chloro-5,5-dimethyl-4-nonanone for 1-chloro-4-nonanone and continuing stirring and heating at 50° for 6 hours, there is obtained 1-chloro-5,5-dimethyl-4-nonanol.

Step 3. Preparation of 1-Chloro-4-acetoxy-5,5-dimethylnonane

By following the procedure described for 1-chloro-4-acetoxynonane (Example A, Step 3) but substituting 1-chloro-5,5-dimethyl-4-nonanol for 1-chloro-4-nonanol and continuing the steam bath heating for 4 hours, there is obtained 1-chloro-4-acetoxy-5,5-dimethylnonane.

H. Preparation of (4S)-1-Methylsulfonyloxy-4-(2-tetrahydropyranyloxy)-nonane

Step 1. Preparation of (3S)-3-(2-Tetrahydropyranyloxy)-1-octyne

A mixture of (3S)-1-octyn-3-ol (63 g., 0.5 mole) and dihydropyran (63 g., 0.75 mole) is cooled to 5° in an ice bath and stirred while concentrated sulfuric acid (0.5 ml.) is added dropwise. The resulting solution is allowed to warm to room temperature and stand for 24 hours. The solution is then treated with solid anhydrous sodium carbonate, filtered, and distilled to yield (3S)-3-(2-tetrahydropyranyloxy)-1-octyne.
* [This optical isomer is described in J. Fried et al., Ann N.Y. Acad. Sci. 180, 38 (1971).]

Step 2. Preparation of (4S)-1,1-Diethoxy-4-(2-tetrahydropyranyloxy)-2-nonyne A solution of ethylmagnesium bromide in 400 ml. of ether is prepared in the usual manner from magnesium (12.2 g., 0.5 mole) and ethyl bromide (56.5 g., 0.52 mole). To this solution, (3S)-3-(2-tetrahydropyranyloxy)-1-octyne (88.2 g., 0.42 mole) is added dropwise with stirring during one hour. The reaction mixture is stirred an additional 45 minutes, and there is added triethyl orthoformate (81.4 g., 0.55 mole) dropwise during 30 minutes. The mixture is then refluxed 16 hours. It is poured into 500 ml. of iced saturated ammonium chloride solution. The oily product is taken up in ether, washed with water, dried over sodium sulfate and distilled to obtain (4S)-1,1-diethoxy-4-(2-tetrahydropyranyloxy)-2-nonyne.

Step 3. Preparation of (4S)-4-Hydroxy-2-nonynal

A mixture of (4S)-1,1-diethoxy-4-(2-tetrahydropyranyloxy)-2-nonyne (96.0 g., 0.31 mole), tetrahydrofuran (500 ml.), and 30% aqueous sulfuric acid (100 ml.) is stirred at room temperature for 17 hours. The solution is diluted with water and the oily product is extracted with ether. The ether extract is washed with sodium bicarbonate solution and water and dried over sodium sulfate. Evaporation of the ether leaves (4S)-4-hydroxy-2-nonynal as a colorless residual oil which is used in the following step without further purification.

Step 4. Preparation of (4S)-4-(2-tetrahydropyranyloxy)-2-nonynal

A mixture of (4S)-4-hydroxy-2-nonynal (41.6 g., 0.27 mole) and dihydropyran (33.6 g., 0.4 mole) is cooled to 5° by means of an ice bath and is treated with 0.2 mole of concentrated sulfuric acid. This is allowed to warm to room temperature and stand 17 hours. It is then diluted with water. The oily product is taken up in ether, washed with sodium bicarbonate solution and water and dried over sodium sulfate. Distillation affords (4S)-4-(2-tetrahydropyranyloxy)-2-nonynal as a colorless oil.

Step 5. Preparation of (4S)-4-(2-tetrahydropyranyloxy)nonanal (4S)-4-(2-Tetrahydropyranyloxy)-2-nonynal (54.6 g., 0.23 mole) in dioxane (200 ml.) is hydrogenated at room temperature and a pressure of 2-3 atmospheres over a 5% palladium on charcoal catalyst to yield (4S)-4-(2-tetrahydropyranyloxy)nonanal purified by distillation at reduced pressure.

Step 6. Preparation of (4S)-4-(2-tetrahydropyranyloxy)-1-nonanol

A solution of (4S)-4-(2-tetrahydropyranyloxy)-nonanal (43.5 g., 0.18 mole) in diglyme (125 ml.) is treated with sodium borohydride (3.8 g., 0.10 mole). The temperature rises to 45° with the resulting exothermic reaction. The solution is stirred 4 hours, acidified with concentrated hydrochloric acid, and concentrated on the rotary evaporator. Water is added to the residue and the oily product is taken up in ether; washed with water and brine and dried over sodium sulfate. Evaporation of the ether leaves (4S)-4-(2-tetrahydropyranyloxy)-1-nonanol as a colorless oil to be used in the next step without further purification.

Step 7. Preparation of (4S)-1-Methylsulfonyloxy-4-(2-tetrahydropyranyloxy)-nonane A mixture of (4S)-4-(2-tetrahydropyranyloxy)-1-nonanol (29.2 g., 0.12 mole) and pyridine (20 ml.) is cooled to 5° by means of an ice bath. Methanesulfonyl chloride (17.2 g., 0.15 mole) is added dropwise during 20 minutes and the mixture is stirred 4 hours with ice bath cooling. The mixture is then taken up in ether, washed with 4 portions of water and with brine and dried over sodium sulfate. The ether is distilled on the rotary evaporator to leave as a residual oil crude (4S)-1-methylsulfonyloxy-4-(2-tetrahydropyranyloxy)-nonane.

I. Preparation of (4R)-1-Methylsulfonyloxy-4-(2-tetrahydropyranyloxy)-nonane

By following the procedure described for (4S)-1-methylsulfonyloxy-4-(2-tetrahydropyranyloxy)-nonane (Example H) but substituting (3R)-1-octyn-3-ol* for (3S)-1-octyn-3-ol there is obtained in succession: (3R)-3-(2-tetrahydropyranyloxy)-1-octyne; (4R)-1,1-diethoxy-4-(2-tetrahydropyranyloxy)-2-nonyne; (4R)-4-hydroxy-2-nonynal; (4R)-4-(2-tetrahydropyranyloxy)-2-nonynal; (4R)-4-(2-tetrahydropyranyloxy)nonanal; (4R)-4-(2-tetrahydropyranyloxy)-1-nonanol; and (4R)-1-methylsulfonyloxy-4-(2-tetrahydropyranyloxy)-nonane.

*This optical isomer is described in R. Pappo, P. Collins, and C. Jung, Ann. N.Y. Acad. Sci. 180, 64 (1971).

J. Preparation of Methyl 7-bromo-2-methylheptanoate

Step 1. Preparation of 5-Acetoxypentyl chloride

Acetic anhydride (102 g., 1 mole) is added dropwise with stirring to pentamethylene chlorohydrin (90 g., 0.74 mole). The resulting solution is heated on the steam bath for one hour and allowed to stand overnight at room temperature. The reaction mixture is distilled to yield 83.6 g. (69%) of 5-acetoxypentyl chloride, b.p. 101°-104°/20 mm.

Step 2. Preparation of Diethyl (5-Acetoxypentyl)methylmalonate

Sodium hydride (4.8 g., 0.2 mole) as a 50% suspension in mineral oil is washed with petroleum ether under nitrogen to remove the mineral oil, suspended in dry benzene (150 ml.), and the suspension cooled in an ice bath. Diethyl methylmalonate (34.8 g., 0.2 mole) dissolved in sieve dried DMF (150 ml.) is added to the suspension of sodium hydride dropwise. The mixture is allowed to stand overnight at room temperature. Potassium iodide (0.4 g.) and 5-acetoxyphenyl chloride (32.9 g., 0.2 mole) are then added, and the mixture is heated for 24 hours at 125° in an oil bath. The reaction mixture is concentrated in vacuo, diluted with ether (200 ml.), and filtered to remove sodium chloride. The filtrate is washed with brine, dried over anhydrous magnesium sulfate and concentrated to yield 39.6 g. (66%) of oily product.

Step 3. Preparation of 7-Bromo-2-methylheptanoic acid

A mixture of the crude diethyl (5-acetoxypentyl)methylmalonate (68 g., 0.23 mole) and 48% aqueous hydrobromic acid (100 ml.) is refluxed for 20 hours. The mixture is then concentrated by distillation until the internal temperature rises to 120°; 96 ml. of distillate (2 layers) is collected. The residual liquid is cooled, dissolved in ether, washed with brine, dried over magnesium sulfate, and the solution concentrated in vacuo to yield 54 g. of crude 7-bromo-2-methylheptanoic acid as a dark viscous liquid.

Step 4. Preparation of Methyl 7-Bromo-2-methylheptanoate

A solution of crude 7-bromo-2-methylheptanoic acid (54 g., 0.24 mole) and concentrated sulfuric acid (2 drops) in absolute methanol (300 ml.) is refluxed for 5 hours. After standing overnight at room temperature, the solution is concentrated in vacuo and diluted with water. The mixture is made basic by the addition of saturated sodium carbonate solution and the product taken up in ether. The ether extract is washed with water, dried over anhydrous magnesium sulfate and distilled to yield 11.8 g. (16%) of methyl 7-bromo-2-methylheptanoate, b.p. 67°-70°/0.05 mm.; pmr (CDCl$_3$)δ1.13 (3H,d 2-CH$_3$), 2.42 (1H,m C$\underline{H}$COOCH$_3$), 3.38 (2H,t CH$_2$Br), 3.65 (3H,s CH$_3$O).

K. Preparation of Ethyl 4-Bromobutoxyacetate

Sodium hydride (9.0 g., 0.375 mole) is suspended in 1,2-dimethoxyethane. The mixture is stirred and cooled in an ice bath while ethyl glycollate (39.0 g., 0.375 mole) is added dropwise during one hour. 1,4-Dibromobutane (108 g., 0.5 mole) is added all at once to the resulting thick suspension. The mixture is warmed gently to initiate a strongly exothermic reaction; then the mixture is heated 3 hours on the steam bath. The mixture is poured into cold water. The heavy oil layer is taken up in ether, washed with three portions of water, and dried over sodium sulfate.

Evaporation of the ether and distillation of the residual oil yields 21.3 g. (24%) of ethyl 4-bromobutoxyacetate, a colorless oil, b.p. 99°-103°/0.2 mm.

EXAMPLE 1

Preparation of 8-Carbamoyl-12-hydroxyheptadecanoic Acid

Step A: Preparation of Di-tert.-Butyl(6-ethoxycarbonylhexyl)malonate

A suspension of 57% sodium hydride in mineral oil (8.84 g. net wt.; 0.21 mole) in a solvent mixture of benzene (95 ml.) and dimethylformamide (95 ml.) is treated, dropwise, over 30 minutes with di-tert.-butylmalonate (41.09 g.; 0.19 mole). Stirring is continued for an additional 30 minutes. Then ethyl 7-bromoheptanoate (49.80 g.; 0.21 mole) is added, dropwise, over 30 min. and the mixture is heated at 100° C. for 4½ hours.

The cooled reaction mixture is treated with water (380 ml.) and the organic layer is separated. The aqueous layer is extracted with ether. The combined organic solutions are washed with saturated sodium chloride solution and then dried over anhydrous sodium sulfate. The solvents are removed under vacuum to give the title compound as a residual oil, yield 70.78 g.

Step B: Preparation of Di-tert.-Butyl 2-(4-acetoxynonyl)-2-(6-ethoxycarbonylhexyl)malonate A suspension of 57% sodium hydride in mineral oil (8.84 g. net wt.; 0.21 mole) in a solvent mixture of benzene (95 ml.) and dimethylformamide (95 ml.) is treated, dropwise, over 30 min., with di-tert.-butyl (6-ethoxycarbonylhexyl)malonate (69.70 g.; 0.187 mole). Stirring is continued for an additional 30 minutes. Then 1-chloro-4-acetoxynonane (46.35 g.; 0.21 mole) (Example A, Step 3) is added, dropwise, over 30 minutes. A trace of potassium iodide is added and the mixture is heated at 100° C. for 42 hours.

The cooled reaction mixture is treated with water (380 ml.) and the organic layer is separated. The aqueous layer is extracted with ether. The combined organic solutions are washed with saturated sodium chloride solution and then dried over anhydrous sodium sulfate. The solvents are removed under vacuum to give the title compound as a residual oil, yield 104.12 g.; pmr (CDCl$_3$)δ0.88 (3H,t), 1.45 (18H,s), 2.00 (3H,s CH$_3$COO), 4.12 (2H,q).

Step C: Preparation of Ethyl 8-Carboxy-12-acetoxyheptadecanoate

A mixture of di-tert.-butyl 2-(4-acetoxynonyl)-2-(6-ethoxycarbonylhexyl)malonate (104.12 g.; 0.187 mole), p-toluenesulfonic acid monohydrate (3.30 g.) and toluene (330 ml.) is heated under reflux for 9½ hrs.

The cooled reaction mixture is washed well with saturated sodium chloride solution and then dried over anhydrous sodium sulfate. The solvent is removed under vacuum to give the title compound as a residual oil, yield 74.90 g. The oil is purified by column chromatography on silica gel with 2% methanol in chloroform as an eluant; pmr $(CDCl_3)\delta 0.88$ (3H,t), 2.02 (3H,s $CH_3COO$), 4.12 (2H,q), 10.97 (1H,s COOH).

Step D: Preparation of Ethyl 8-Chlorocarbonyl-12-acetoxyheptadecanoate

A solution of ethyl 8-carboxy-12-acetoxyheptadecanoate (12.0 g.; 0.03 mole) and thionyl chloride (7.2 g.; 0.06 mole) in benzene (50 ml.) is boiled under reflux for 2½ hours.

The volatile materials are removed under vacuum in a rotary evaporator leaving the product as an orange oil weighing 12.5 g. (100%); ir (neat) 1790 (acid chloride C=O), 1730 cm$^{-1}$ (ester C=O). This crude product is used directly in the next step.

Step E: Preparation of Ethyl 8-Carbamoyl-12-acetoxyheptadecanoate

Ethyl 8-chlorocarbonyl-12-acetoxyheptadecanoate (8.38 g.; 0.02 mole) is added with stirring to a 28% solution of ammonia in water (concentrated ammonium hydroxide) (75 ml.). The amide forms at once and separates as a semi-solid. It is dissolved in ether, washed with water and dried over sodium sulfate. The ether is removed under vacuum to give the title compound as a semi-solid, yield 6.8 g. The product is purified by column chromatography on silica gel with 2% methanol in chloroform as eluant; pmr $(CDCl_3)\delta 0.88$ (3H,t), 2.02 (3H,s $CH_3COO$), 4.12 (2H,q), 4.85 (1H,m HCO), 5.98 (2H,s $NH_2$).

Anal. Calcd. for $C_{22}H_{41}NO_5$: C, 66.13; H, 10.34; N, 3.51. Found: C, 66.12; H, 10.74; N, 3.42.

Step F: Preparation of 8-Carbamoyl-12-hydroxyheptadecanoic Acid

Ethyl 8-carbamoyl-12-acetoxyheptadecanoate (5.50 g., 0.0138 mole) is added to a solution of sodium hydroxide (1.66 g., 0.0414 mole) in water (8 ml.) and methanol (72 ml.). The resulting solution is allowed to stand 24 hours at 25° C.

Most of the methanol is then evaporated in vacuo. The residual solution is diluted with water (80 ml.), extracted once with ether, and acidified with concentrated hydrochloric acid to the Congo red endpoint. The resulting oil is dissolved in ether, washed well with water and dried over anhydrous sodium sulfate. The ether is removed under vacuum to give the title compound as a yellow oil, yield 3.60 g. (80%), which gradually solidifies, m.p. 74°–78° C.; pmr $(CDCl_3)\delta 0.88$ (3H,t) 3.55 (1H,m HCO), 6.53 (1H,s NH), 6.88 (1H,s NH), 7.80 (2H,s OH,COOH).

Anal. Calcd. for $C_{18}H_{35}NO_4$: C, 65.62; H, 10.71; N, 4.25. Found: C, 65.63, H, 10.95; N, 3.93.

EXAMPLE 2

Preparation of 8-Methylcarbamoyl-12-hydroxyheptadecanoic Acid

The synthesis of this compound is carried out as described in Example 1, except that in Step E, 75 ml. of a 40% solution of methylamine in water is substituted for the solution of ammonia in water. Thus, there is obtained: ethyl 8-methylcarbamoyl-12-acetoxyheptadecanoate (Step E), and 8-methylcarbamoyl-12-hydroxyheptadecanoic acid (Step F).

EXAMPLE 3

Preparation of 8-Ethylcarbamoyl-12-hydroxyheptadecanoic Acid

The synthesis of this compound is carried out as described in Example 1, except that in Step E, 40 ml. of a 70% solution of ethylamine in water is substituted for the solution of ammonia in water. Thus, there is obtained: ethyl 8-ethylcarbamoyl-12-acetoxyheptadecanoate (Step D), and 8-ethylcarbamoyl-12-hydroxyheptadecanoic acid (Step F).

EXAMPLE 4

Preparation of 8-Propylcarbamoyl-12-hydroxyheptadecanoic Acid

The synthesis of this compound is carried out as in Example 1, except that in Step E, 50 ml. of a 40% solution of propylamine in water is substituted for the solution of ammonia in water. Thus, there is obtained: ethyl 8-propylcarbamoyl-12-acetoxyheptadecanoate (Step E), and 8-propylcarbamoyl-12-hydroxyheptadecanoic acid (Step F).

EXAMPLE 5

Preparation of 8-Dimethylcarbamoyl-12-hydroxyheptadecanoic Acid

The synthesis of this compound is carried out as described in Example 1, except that in Step E, 75 ml. of a 25% solution of dimethylamine in water is substituted for the solution of ammonia in water. Thus, there is obtained: ethyl 8-dimethylcarbamoyl-12acetoxyheptadecanoate (Step E), and 8-dimethylcarbamoyl-12-hydroxyheptadecanoic acid (Step F).

EXAMPLE 6

Preparation of 8-Ethylmethylcarbamoyl-12-hydroxyheptadecanoic Acid

The synthesis of this compound is carried out as described in Example 1, except that in Step E, 60 ml. of a 25% solution of ethylmethylamine in water is substituted for the solution of ammonia in water. Thus, there is obtained: ethyl 8-ethylmethylcarbamoyl-12-acetoxyheptadecanoate (Step E), and 8-ethylmethylcarbamoyl-12-hydroxyheptadecanoic acid (Step F).

EXAMPLE 7

Preparation of 8-Carbamoyl-12-hydroxy-16-methylheptadecanoic Acid

The synthesis of this compound is carried out as described in Example 1 except that, in Step B, the 1-chloro-4-acetoxynonane is replaced by an equimolar amount of 1-chloro-4-acetoxy-8-methylnonane (Example B, Step 3). The product of Step B is thus di-tert.-butyl 2-(4-acetoxy-8-methylnonyl)-2-(6-ethoxycarbonylhexyl)-malonate. Subsequent steps yield: ethyl 8-carboxy-12-acetoxy-16-methylheptadecanoate (C); ethyl 8-chlorocarbonyl-12-acetoxy-16-methylheptadecanoate (D); ethyl 8-carbamoyl-12-acetoxy-16-methylheptadecanoate (E); and 8-carbamoyl-12-hydroxy-16-methylheptadecanoic acid (F).

EXAMPLE 8

Preparation of 8-Carbamoyl-12-hydroxynonadecanoic Acid

The synthesis of this compound is carried out as described in Example 1, except that, in Step B, the 1-chloro-4-acetoxynonane is replaced by an equimolar amount of 1-chloro-4-acetoxyundecane (Example C, Step 3). The product of Step B is thus di-tert.-butyl 2-(4-acetoxyundecyl)-2-(6-ethoxycarbonylhexyl)malonate. Subsequent steps yield: ethyl 8-carboxy-12-acetoxynonadecanoate (C); ethyl 8-chlorocarbonyl-12-acetoxynonadecanoate (D); ethyl 8-carbamoyl-12-acetoxynonadecanoate (E); and 8-carbamoyl-12-hydroxynonadecanoic acid (F).

EXAMPLE 9

Preparation of 8-Carbamoyl-12-hydroxy-16,16-dimethylheptadecanoic Acid

The synthesis of this compound is carried out as described in Example 1, except that, in Step B, the 1-chloro-4-acetoxynonane is replaced by an equimolar amount of 1-chloro-4-acetoxy-8,8-dimethylnonane (Example D, Step 3). The product of Step B is thus di-tert.-butyl 2-(4-acetoxy-8,8-dimethylnonyl)-2-(6-ethoxycarbonylhexyl)-malonate. Subsequent steps yield: ethyl 8-carboxy-12-acetoxy-16,16-dimethylheptadecanoate (C); ethyl 8-chlorocarbonyl-12-acetoxy-16,16-dimethylheptadecanoate (D); ethyl 8-carbamoyl-12-acetoxy-16,16dimethylheptadecanoate (E); and 8-carbamoyl-12-hydroxy16,16dimethylheptadecanoic acid (F).

EXAMPLE 10

Preparation of 8-Carbamoyl-12-hydroxy-17,17,17-trifluoroheptadecanoic Acid

The synthesis of this compound is carried out as described in Example 1 except that, in Step B, the 1-chloro-4-acetoxynonane is replaced by an equimolar amount of 1-chloro-4-acetoxy-9,9,9-trifluorononane (Example E, Step 3). The product of Step B is thus di-tert.-butyl 2-(4-acetoxy-9,9,9-trifluorononyl)-2-(6-ethoxycarbonylhexyl)malonate. Subsequent steps yield: ethyl 8carboxy-12-acetoxy-17,17,17-trifluoroheptadecanoate (C); ethyl 8-chlorocarbonyl-12-acetoxy-17,17,17-trifluoroheptadecanoate (D); ethyl 8-carbamoyl-12-acetoxy-17,17,17-trifluoroheptadecanoate (E); and 8-carbamoyl-12-hydroxy-17,17,17-trifluoroheptadecanoic acid.

EXAMPLE 11

Preparation of 8-Carbamoyl-12-hydroxy-16heptadecanoic Acid

The synthesis of this compound is carried out as described in Example 1, except that, in Step B, the 1-chloro-4-acetoxynonane is replaced by an equimolar amount of 1-chloro-4-acetoxy-8-nonene (Example F, Step 3). The product of Step B is thus di-tert.-butyl 2-(4-acetoxy-8-nonen-1-yl)-2-(6-ethoxycarbonylhexyl)-malonate. Subsequent steps yield: ethyl 8-carboxy-12-acetoxy-16-heptadecenoate (C); ethyl 8-chlorocarbonyl-12-acetoxy-16-heptadecanoate (D); ethyl 8-carbamoyl-12-acetoxy-16-heptadecanoate (E); and 8-carbamoyl-12-hydroxy-16-heptadecenoic acid (F).

EXAMPLE 12

Preparation of 8-Carbamoyl-12-hydroxy-13,13-dimethylheptadecanoic Acid

The synthesis of this compound is carried out as described in Example 1, except that, in Step B, the 1-chloro-4-acetoxynonane is replaced by an equimolar amount of 1-chloro-4-acetoxy-5,5-dimethylnonane (Example G, Step 3). The product of Step B is thus: di-tert.-butyl 2(4-acetoxy-5,5-dimethylnonyl)-2-(6-ethoxycarbonylhexyl)malonate. Subsequent steps yield: ethyl 8-carboxy-12-acetoxy-13,13-dimethylheptadecanoate (C); ethyl 8-chlorocarbonyl-12-acetoxy-13,13-dimethylheptadecanoate (D); ethyl carbamoyl-12-acetoxy-13,13-dimethylheptadecanoate (E); and 8-carbamoyl-12-hydroxy-13,13-dimethylheptadecanoic acid (F).

EXAMPLE 13

Preparation of 8-Carbamoyl-12-(S)-hydroxyheptadecanoic Acid

Step A: Preparation of Di.-tert.-butyl 2-[4-(S)-(2-tetrahydropyranyloxy)-nonyl]-2-(ethoxycarbonylhexyl)malonate The synthesis of this compound is caarried out as described in Example 1 with several modifications of procedure. In Step B, the 1-chloro-4-acetoxynonane is replaced by an equimolar amount of (4S)-1-methylsulfonyloxy-4(2-tetrahydroyranyloxy)nonane (Example H, Step 7). The product of Step B is thus di-tert.-butyl 2-[4-(S)-(2-tetrahydropyranyloxy)nonyl]-2-(6-ethoxycarbonylhexyl)malonate.

Two additional steps, B-1 and B-2, are added at this point.

Step B-1: Preparation of Di-tert.-butyl 2-[4-(S)-hydroxynonyl]-2-(6-ethoxycarbonylhexyl)malonate Di-tert.-butyl 2-[4(S)-(2-tetrahydropyranyloxy)-nonyl]-2-(6-ethoxycarbonylhexyl)malonate (47.8 g., 0.08 mole) is added to a mixture of tetrahydrofuran (300 ml.) and 6N hydrochloric acid (15 ml.). The resulting solution is allowed to stand at room temperature for 6 hours. The solution is then diluted with 1.5 liters of water. The oily product is taken up in ether, washed with four portions of water, and with brine and dried over sodium sulfate. Distillation of the ether in vacuo leaves the title compound as a residual oil weighing 39.5 g.

Step B-2: Preparation of Di-tert.-butyl-2[4-(S)-acetoxynonyl]-2-(6-ethoxycarbonylhexyl)malonate Di-tert.-butyl 2-[4-(S)-hydroxynonyl]-2-(6-ethoxycarbonylhexyl)malonate (39.0 g., 0.076 mole) is dissolved in pyridine (50 ml.). Acetic anhydride (8.2 g., 0.08 mole) is added dropwise during 15 minutes and the mixture is stirred and heated at 60° C. for 3 hours. The mixture is then cooled and treated with 300 ml. water. The oily product is taken up in ether, washed with 5% hydrochloric acid, two portions of water and brine, and dried over sodium sulfate. Distillation of the ether in vacuo leaves the title compound as a residual oil weighing 41 g.

The remainder of the synthesis is conducted exactly as in Example 1, Steps C, D, E, and F. There is obtained in succession: ethyl 8-carboxy-12-(S)-acetoxyheptadecanoate (C); ethyl 8-chlorocarbonyl-12-(S)-acetoxyheptadecanoate (D); ethyl 8-carbamoyl-12-(S)-acetoxyheptadecanoate (E); and ethyl 8-carbamoyl-12-(S)-hydroxyheptadecanoic acid (F).

EXAMPLE 14

Preparation of 8-Carbamoyl-12-(R)-hydroxyheptadecanoic Acid

The synthesis of this compound is carried out exactly according to the procedure described for the 12-(S) compound of Example 13 except that in Step B, the (4S)-1-methylsulfonyloxy-4-(2-tetrahydropyranyloxy)-nonane is replaced by an equimolar amount of (4R)-1-methylsulfonyloxy-4-(2-tetrahydropyranyloxy)nonane (Example I, Step 7). The product of Step B is thus di-tert.-butyl 2-[4-(2-tetrahydropyranyloxy)nonyl]-2-(6-ethoxycarbonylhexyl)malonate. Subsequent steps yield: di-tert.-butyl 2-(4-(R)-hydroxynonyl)-2-(6ethoxycarbonylhexyl)malonate (B-1); di-tert.-butyl 2-(4-(R)-acetoxynonyl)-2-(6-ethoxycarbonylhexyl)malonate (B-2); ethyl 8-carboxy-12-(R)-acetoxyheptadecanoate (C); ethyl 8-chlorocarbonyl-12-(R)-acetoxyheptadecanoate (D); ethyl 8-carbamoyl-12-(R)-acetoxyheptadecanoate (E); and 8-carbamoyl-12-(R)-hydroxheptadecanoic acid (F).

EXAMPLE 15

Preparation of 8-Carbamoyl-12-hydroxy-2-methylheptadecanoic Acid

The synthestis of this compound is carried out as described in Example 1 except that, in Step A, the ethyl 7-bromoheptanoate is replaced by an equimolar amount of methyl 7-bromo-2-methylheptanoate (Example J, Step 4). The product of Step A is thus di-tert.-butyl (6-methoxycarbonyl-6-methylhexyl)malonate. Subsequent steps yield: di-tert.-butyl 2-(4-acetoxynonyl)-2-(6-methoxycarbonyl-6-methylhexyl)malonate (B); methyl 8-carboxy-12 -acetoxy-2-methylheptadecanoate (C); methyl 8-chlorocarbonyl-12-acetoxy-2-methylheptadecanoate (D); methyl 8-carbamoyl-12-acetoxy-2-methylheptadecanoate (E); and 8-carbamoyl-12-hydroxy-2-methylheptadecanoic acid (F).

EXAMPLE 16

Preparation of 8-Carbamoyl-12-hydroxy-3-methylheptadecanoic Acid

The synthesis of this compound is carried out as described in Example 1 except that, in Step A, the ethyl 7-bromoheptanoate is replaced by an equimolar amount of methyl 3-methyl-7-iodoheptanoate. The product of Step A is thus: di-tert.-butyl (6-methoxycarbonyl-5-methylhexyl)malonate. Subsequent steps yield: di.-tert.-butyl 2-(4-acetoxynonyl)-2-(6-methoxycarbonyl-5-methylhexyl)malonate (D); methyl 8carboxy-12-acetoxy-3-methylheptadecanoate (V); methyl 8-chlorocarbonyl-12-acetoxy-3-methylheptadecanoate (D); methyl 8-carbamoyl-12-acetoxy-3-methylheptadecanote (E); and 8carbamoyl-12-acetoxy-3-methylheptadecanoic acid (F).

EXAMPLE 17

Preparation of 8-Carbamoyl-12-hydroxy-2,2-dimethylheptadecanoic Acid

The synthesis of this compound is carried out as described in Example 1, except that, in Step A, the ethyl 7-bromoheptanoate is replaced by an equimolar amount of methyl 2,2-dimethyl-7-iodoheptanoate. The product of Step A is thus di-tert.-butyl (6-methoxycarbonyl-6,6-dimethylhexyl)malonate. Subsequent steps yield: di-tert.-butyl 2(4-acetoxynonyl)-2-(6-methoxycarbonyl-6,6-dimethylhexyl)malonate (B); methyl 8-carboxy12-acetoxy-2,2-dimethylheptadecanoate (C); methyl 8chlorocarbonyl-12-acetoxy-2,2-dimethylheptadecanoate (D); methyl 8-carbamoyl-12-acetoxy-2,2-dimethylheptadecanoate (E); and 8-carbamoyl-12-hydroxy-2,2-dimethylheptadecanoic acid (F).

EXAMPLE 18

Preparation of 8-Carbamoyl-12-hydroxy-3,3-dimethylheptadecanoic Acid

The synthesis of this compound is carried out as described in Example 1 except that, in Step A, the ethyl 7-bromoheptanoate is replaced by an equimolar amount of methyl 3,3-dimethyl-7-iodoheptanoate. The product of Step A is thus di-tert.-butyl (6-methoxycarbonyl-5,5-dimethylhexyl)malonate. Subsequent steps yield: di-tert.-butyl 2-(4-acetoxynonyl)-2(6-methoxycarbonyl-5,5-dimethylhexyl)malonate (B); methyl 8-carboxy-12-acetoxy-3,3-dimethylheptadecanoate (C); methyl 8-chlorocarbonyl-12-acetoxy-3,3-dimethylheptadecanoate (D); methyl 8carbamoyl-12-acetoxy-3,3dimethylheptadecanoate (E); and 8-carbamoyl-12-hydroxy3,3-dimethylheptadecanoic acid (F).

EXAMPLE 19

Preparation of 5-Carbamoyl-9-hydroxytetradecyloxyacetic Acid

The synthesis of this compound is carried out as described in Example 1 except that, in Step A, the ethyl 7-bromoheptanoate is replaced by an equimolar amount of ethyl 4-bromobutoxyacetate (Example K). The product of Step A is thus di-tert.-butyl (4-ethoxycarbonylmethoxybutyl)malonate. Subsequent steps yield: di-tert.-butyl 2-(4-acetoxynonyl)-2-(4-ethoxycarbonylmethoxybutyl)-malonate (B); ethyl 5-carboxy-9-acetoxytetradecyloxyacetate (C); ethyl 5-chlorocarbonyl-9-acetoxytetradecyloxyacetate (D); ethyl 5-carbamoyl-9-acetoxytetradecyloxyacetate (E); and 5-carbamoyl-9-hydroxytetradecyloxyacetic acid (F).

EXAMPLE 20

Preparation of 8-Carbamoyl-12-hydroxy-12-methylheptadecanoic Acid

Step A: Preparation of Di-tert.-butyl (6-ethoxycarbonylhexyl)malonate

The synthesis of this compound is described in Example 1, Step A.

Step B: Preparation of Di-tert.-butyl 2-(4-methyl-3-nonen-1-yl)-2-(6-ethoxycarbonylhexyl)-malonate The synthesis of this compound is carried out as described in Example 1, Step B, except that the 1-chloro-4-acetoxynonane is replaced by an equimolar amount of 1-chloro-4-methyl-3-nonene.

Step C: Preparation of Ethyl 8-carboxy-12-methyl-11-heptadecenoate

The synthesis of this compound is carried out as described in Example 1, Step C, except that the product of Example 20 of Step B replaces the di-tert.-butyl 2-(4-acetoxynonyl)-2-(6-ethoxycarbonylnonyl)malonate of the Example 1, Step C.

Step D: Preparation of Ethyl 8-Chlorocarbonyl-12-methyl-11-heptadecenoate

The synthesis of this compound is carried out as described in Example 1, Step D, except that ethyl 8-carboxy-12-acetoxyheptadecanoate is replaced by an equimolar amount of ethyl 8-carboxy-12-methyl-11-heptadecenoate.

Step E: Preparation of Ethyl 8-Carbamoyl-12-methyl-11-heptadecenoate

The synthesis of this compound is carried out as described in Example 1, Step E, except that ethyl 8-chlorocarbonyl-12-acetoxyheptadecanoate is replaced by an equimolar amount of ethyl 8-chlorocarbonyl-12-methyl-11-heptadecenoate.

Step F: Preparation of Ethyl 8-Carbamoyl-12-hydroxy-12-methylheptadecanoate

Mercuric acetate (3.8 g., 0.012 mole) is dissolved in water (12 ml.) and tetrahydrofuran (20 ml.) is added to give a suspension of a yellow solid. Then, ethyl 8-carbamoyl-12-methyl-11-heptadecenoate (4.2 g., 0.012 mole) in tetrahydrofuran (20 ml.) is added, and the mixture stirred at room temperature for 24 hours. After 6 hours, the yellow suspended solid has disappeared and a cloudy solution results. To the solution is added 3M sodium hydroxide solution (12 ml.), followed by 0.5M sodium borohydride solution in 3M sodium hydroxide (12 ml.). Liquids are decanted from the precipitated mercury. The organic layer is taken up in ether, washed with three portions of water and dried over sodium sulfate. Evaporation of the ether leaves 4.0 g. of ethyl 8-carbamoyl-12-hydroxy-12-methylheptadecanoate which is used in the next step without further purification.

Step G: preparation of 8-Carbamoyl-12-hydroxy-12-methylheptadecanoic Acid

The synthesis of this compound is carried out as described in Example 1, Step F, except that the ethyl 8-carbamoyl-12-acetoxyheptadecanoate is replaced by an equimolar amount of ethyl 8-carbamoyl-12-hydroxy-12-methylheptadecanoate.

EXAMPLE 21

Preparation of 8-Carbamoyl-12-acetoxyheptadecanoic Acid

A mixture of 8-carbamoyl-12-hydroxyheptadecanoic acid (8.2 g., 0.025 mole) (Example 1, Step F) and acetic anhydride (6.1 g., 0.06 mole) is heated at 60° C. for 18 hours. The mixture is then cooled and dissolved in 80 ml. ethyl ether. The solution is extracted with an ice-cold solution of 8 g. sodium hydroxide in 150 ml. water. The basic solution is separated and acidified with concentrated hydrochloric acid. The oily acid which separates is taken up in ether, washed with water and dried over sodium sulfate. The ether is evaporated to leave 9.0 g. of the oily crude product.

The product is purified by chromatography on a column containing 150 g. of silica gel and with 2% methanol in chloroform as the eluting solvent. There is obtained 5.5 g. of 8-carbamoyl-12-acetoxyheptadecanoic acid, a colorless viscous oil.

By substituting the acetic anhydride used in Example 22 with an equivalent amount of propionic anhydride, butyric anhydride, isobutyric anhydride, valeric anhydride, or pivalic anhydride and conducting the reaction as described in Example 21, there is obtained 8-carbamoyl-12-propionyloxyheptadecanoic acid, 8-carbamoyl-12-butyryloxyheptadecanoic acid, 8-carbamoyl-12-isobutyryloxyheptadecanoic acid, 8-carbamoyl-12-valeryloxyheptadecanoic acid, and 8-carbamoyl-12-pivaloyloxyheptadecanoic acid, respectively.

EXAMPLE 22

Preparation of 8-Carbamoyl-12-formyloxyheptadecanoic Acid

A mixture of 8-carbamoyl-12-hydroxyheptadecanoic acid (8.2 g., 0.025 mole) (Example 1, Step F) and 97% formic acid (10 ml.) is heated at 60° C. for 24 hours. The mixture is cooled, dissolved in 100 ml. ether, washed with 3 portions of water and dried over sodium sulfate. Evaporation of the ether leaves the product 8-carbamoyl-12-formyloxyheptadecanoic acid as a slightly yellowish viscous oil.

EXAMPLE 23

Preparation of Methyl 8-Carbamoyl-12-hydroxyheptadecanoate

A solution of diazomethane (approx. 2.5 g., 0.06 mole) in ether (100 ml.) is mixed with a solution of 8-carbamoyl-12-hydroxyheptadanoic acid (9.9 g., 0.03 mole) (Example 1, Step F), in ether (50 ml.). The resulting solution is allowed to stand 4 hours at room temperature. Acetic acid is the added to destroy the excess diazomethane and the solution is washed with dilute sodim bicarbonate solution and water and dried over sodium sulfate. Evaporation of volatile materials at reduced pressure yields methyl 8-carbamoyl-12-hydroxyheptadecanoate, a colorless viscous oil.

EXAMPLE 24

Preparation of Decyl 8-Carbamoyl-12-hydroxyheptadecanoate

Using the method of Example 23 but substituting an ether solution 1-diazodecane for the ether solution of diazomethane there is obtained decyl 8-carbamoyl-12-hydroxyheptadecanoate, a colorless viscous oil.

EXAMPLE 25

Preparation of N-[(2-Dimethylamino)ethyl]-8-carbamoyl-12-hydroxyheptadecanamide

A solution of 8-carbamoyl-12-hydroxyheptadecanoic acid (3.29 g., 10 millimole) (Example 1, Step F) triethylamine (1.74 ml., 12.5 millimole) and distilled water (18 ml., 1.0 mole) in acetonitrile (100 ml.) is treated with N-t-butyl-5-methylisoxazolium perchlorate (3.0 g., 12.5 millimole). The resulting solution is evaporated in vacuo (water aspirator) at 20-23° C. for 4 hours providing a tacky residue which is triturated with water (150 ml.) at 0°-5° C. for 15 minutes. After decanting the aqueous phase, the oily residue is dissolved in benzene-ether [(1:1), 200 ml.]. The organic extract is dried over sodium sulfate, filtered and evaporated in vacuo at 35°-40° C. providing the desired "active ester", N-t-butyl-3-(8-carbamoyl-12-hydroxyheptadecanoyloxy)-crotonamide, as a pale yellow oil.

A solution of 2-dimethylaminoethylamine (0.88 g., 10 millimole) in acetonitrile (25 ml.) is added to the solution of the "active ester" in acetonitrile (25 ml.) providing a clear solution which is stirred at 25° C. for 17 hours. The solvent is removed in vacuo at 40°-50° C. leaving a residual oil which is partitioned between ether (200 ml.) and water (2 × 100 ml.). The organic extract is washed with saturated brine (2 × 100 ml.), dried over sodium sulfate, filtered and evaporated in vacuo at 40°-50° C. providing a tan, crude oil.

The oil is partitioned between 5% hydrochloric acid (100 ml.) and ether (2 × 100 ml.). The aqueous acid phase is slowly basified with sodium bicarbonate (16.8 g., 0.2 mole), then with 40% aqueous sodium hydroxide (10 ml.) providing a heterogeneous mixture which is extracted with ether (200, 100 ml.). The organic extract is washed with saturated brine (200 ml.), dried over sodium sulfate, filtered and evaporated in vacuo at 40°-50° C. leaving the title compound as a pale yellow oil.

EXAMPLE 26

Preparation of 8-Carbamoyl-12-hydroxyheptadecanoic Acid Hydrazide

This compound is prepared essentially by the same procedure as described in Example 25 except hydrazine is used rather than an aliphatic amine and the acid-hydrazine conjugation is effected at −15° C. employing the following reagents:

8Carbamoyl-12-hydroxy heptadecanoic acid (Example 1, Step F): 3.29 g., 0.01 mole
Triethylamine: 1.74 ml., 0.0125 mole
Distilled water: 18 ml., 1.0 mole
N-t-Butyl-5-methyl-isoxazolium perchlorate: 3.0 g., 0.0125 mole
Acetonitrile: 150 ml.
Hydrazine.hydrate: 0.5 g., 0.01 mole
The title compound is obtained as a pale yellow oil.

What is claimed is:

1. The compound having the following formula:

$$R^1-N(R^2)-C(=O)-C(H)(\text{(CH}_2\text{)}_3-C(R^3)(R^5)(OR^4))-(CH_2)_4-A-R$$

wherein

R is carboxy or a carboxy salt having the formula —COO⁻Me⁺ wherein Me is a pharmaceutically-acceptable cation derived from a metal or an amine;
A is ethylene, trimethylene, α-methylethylene, β-methylethylene, α,α-dimethylethylene, or β,β-dimethylethylene;
R¹ is hydrogen or methyl;
R² is hydrogen or alkyl or 1-3 carbon atoms;
R³ is hydrogen or methyl;
R⁴ is hydrogen; and
R⁵ is loweralkyl of 3-7 carbon atoms, 4-pentenyl, or 5,5,5-trifluoropentyl; except that when R³ is methyl, R⁵ is limited to propyl, butyl, pentyl, 4-methylpentyl, 4,4-dimethylpentyl, hexyl, heptyl, and 5,5,5-trifluoropentyl.

2. The compound of claim 1 which has the formula:

$$R^1-N(R^2)-C(=O)-C(H)(\text{(CH}_2\text{)}_3-C(H)(R^5)(OH))-(CH_2)_4-A-COOH$$

wherein

A is ethylene, α-methylethylene, β-methylethylene, trimethylene, α,α-dimethylethylene, or β,β-dimethylethylene;
R¹ is hydrogen or methyl;
R² is hydrogen or alkyl having 1-3 carbon atoms; and
R⁵ is loweralkyl of 3-7 carbon atoms, 4-pentenyl, or 5,5,5-trifluoropentyl.

3. The compound of claim 1 which has the formula:

$$R^1-N(R^2)-C(=O)-CH(\text{(CH}_2\text{)}_3-C(CH_3)(R^{10})(OH))-(CH_2)_4-A-COOH$$

wherein

A is ethylene, trimethylene, α-methylethylene, β-methylethylene, α,α-dimethylethylene, or β,β-dimethylethylene;
R¹ is hydrogen or methyl;
R² is hydrogen or alkyl having 1-3 carbon atoms; and
R¹⁰ is loweralkyl of 3-7 carbon atoms or 5,5,5-trifluoropentyl.

4. The compound of claim 2 wherein A is α-methylethylene, R¹ and R² are hydrogen and R⁵ is pentyl, that is, 8-carbamoyl-12-hydroxy-2-methyl-heptadecanoic acid.

5. The compound of claim 2 wherein A is β,β-dimethylethylene, R¹ and R² are hydrogen and R⁵ is pentyl, that is, 8-carbamoyl-12-3,3-dimethyl-heptadecanoic acid.

6. The compound of claim 2 wherein A is ethylene, R¹ and R² are hydrogen and R⁵ is pentyl, that is, 8-carbamoyl-12-hydroxyheptadecanoic acid.

7. The compound of claim 2 wherein A is ethylene, R¹ is hydrogen, R² is methyl and R⁵ is pentyl, that is, 8-methylcarbamoyl-12-hydroxyheptadecanoic acid.

8. The compound of claim 2 wherein A is ethylene, R¹ and R² are hydrogen and R⁵ is 4-methylpentyl, that is, 8-carbamoyl-12-hydroxy-16-methylheptadecanoic acid.

9. The compound of claim 2 wherein A is ethylene, R¹ and R² are hydrogen and R⁵ is heptyl, that is, 8-carbamoyl-12-hydroxynonadecanoic acid.

10. The compound of claim 2 wherein A is ethylene, R¹ and R² are hydrogen and R⁵ is 5,5,5-trifluoropentyl, that is, 8-carbamoyl-12-hydroxy-17,17,17-trifluoroheptadecanoic acid.

11. The compound of claim 2 wherein A is ethylene, R¹ and R² are hydrogen and R⁵ is 1,1-dimethylpentyl, that is, 8-carbamoyl-12-hydroxy-13,13-dimethylheptadecanoic acid.

12. The compound of claim 2 wherein A is ethylene, $R^1$ and $R^2$ are hydrogen, $R^5$ is pentyl and the 12-carbon is in the S configuration, that is, 8-carbamoyl-12(S)-hydroxyheptadecanoic acid.

13. The compound of claim 2 wherein A is ethylene, $R^1$ and $R^2$ are hydrogen, $R^5$ is pentyl and the 12-carbon atom is in the R configuration, that is, 8-carbamoyl-12(R)-hydroxyheptanoic acid.

14. The compound of claim 3 wherein A is ethylene, $R^1$ and $R^2$ are hydrogen and $R^{10}$ is pentyl, that is, 8-carbamoyl-12-hydroxy-12-methylheptadecanoic acid.

* * * * *

UNITED STATES PATENT OFFICE
CERTIFICATE OF CORRECTION

PATENT NO. : 4,055,597
DATED : October 25, 1977
INVENTOR(S) : Edward J. Cragoe, Jr. and John B. Bicking It is certified that error appears in the above-identified patent and that said Letters Patent are hereby corrected as shown below:

Column 28, Line 1, after the word, "alkyl", delete the word, "or", and substitute therefor -- of --.

Column 28, Line 49, after "8-carbamoyl-12-" and before "3,3-dimethyl...", insert -- hydroxy- --.

Signed and Sealed this

Twenty-first Day of February 1978

[SEAL]

Attest:

RUTH C. MASON
Attesting Officer

LUTRELLE F. PARKER
Acting Commissioner of Patents and Trademarks